United States Patent
Dall'asta et al.

(10) Patent No.: US 7,166,729 B2
(45) Date of Patent: Jan. 23, 2007

(54) PROCESS FOR THE PREPARATION OF 5-SUBSTITUTED ISOBENZOFURANS

(75) Inventors: Leone Dall'asta, Milan (IT); Giovanni Cotticelli, Cernusco sul Naviglio (IT)

(73) Assignee: Infosint SA, Cantoni Dei Grigioni (CH)

( * ) Notice: Subject to any disclaimer, the term of this patent is extended or adjusted under 35 U.S.C. 154(b) by 0 days.

(21) Appl. No.: 10/776,625

(22) Filed: Jan. 31, 2004

(65) Prior Publication Data

US 2004/0230065 A1 Nov. 18, 2004

Related U.S. Application Data

(63) Continuation of application No. PCT/EP02/08550, filed on Jul. 29, 2002.

(51) Int. Cl.
*C07D 307/87* (2006.01)

(52) U.S. Cl. .................................................. 549/467

(58) Field of Classification Search ................ 549/442, 549/467

See application file for complete search history.

(56) References Cited

FOREIGN PATENT DOCUMENTS

WO        02/48133 A2 *   6/2002

* cited by examiner

*Primary Examiner*—Taofiq Solola
(74) *Attorney, Agent, or Firm*—Katten Muchin Rosenman LLP

(57) ABSTRACT

There is described a process for the preparation of citalopram and of its pharmaceutically acceptable salts, which comprises treating a 1-[3-(dimethylamino)propyl]-1-(4-fluorophenyl)-1,3-dihydro-5 isobenzofurancarbaldoxime, O-substituted preferably with a diphenylmethyl or triphenylmethyl group, with formic-acetic anhydride. Furthermore, the total synthesis of citalopram, as free base or in form of its pharmaceutically acceptable salt, starting from 5-formylphthalide is described.

22 Claims, No Drawings

PROCESS FOR THE PREPARATION OF 5-SUBSTITUTED ISOBENZOFURANS

CROSS-REFERENCE TO RELATED APPLICATION

The present application is a continuation of International Application No. PCT/EP02/08550 which was filed on Jul. 29, 2002.

The present invention relates to a process for the preparation of citalopram and, more particularly, to a process for the preparation of citalopram stating from 5-formylphthalide.

Citalopram, or 1-[3-(dimethylamino)propyl]-1-(4-fluorophenyl)-1,3 dihydro-5-isobenzofurancarbonitrile, represented by the formula

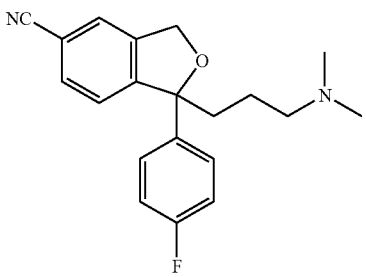

(A)

is an active substance used as hydrobromide, for the preparation of pharmaceutical compositions indicated for the treatment of depression.

Citalopram has been described for the first time in Belgian patent 850,401 and afterwards, various methods for its preparation have been disclosed.

For example, EP 171943 describes the preparation of a diol, precursor of citalopram, of formula

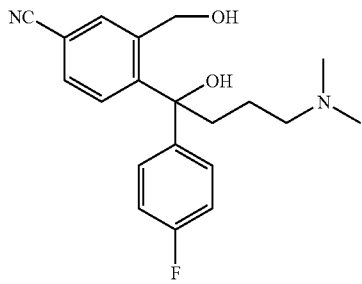

(B)

obtainable, starting from 5-cyanophthalide, by two subsequent Grignard reactions, one with 4-fluorophenyl magnesium bromide and the second one, on the obtained magnesium derivative, with [3-(dimethylamino)propyl] magnesium bromide. The cyano group, however, being not inert towards halomagnesium reactants, gives rise to reaction by-products which are difficult to separate.

Patent application WO 01/02383 describes a method for the preparation of citalopram which consists of transforming the 1-[3-dimethylamino)propyl]-1-(4-fluorophenyl)-5-bromo-1,3-dihydroisobenzofuran into the magnesium derivative in 5-position, of submitting the Grignard reactant thus obtained to a reaction with a formamide to give the 1-[(3-dimethylamino)propyl]-1-(4-fluorophenyl)-1,3-dihydro-5-isobenzofurancarboxaldehyde, in treating this last compound with hydroxylamine and converting the compound thus obtained of formula

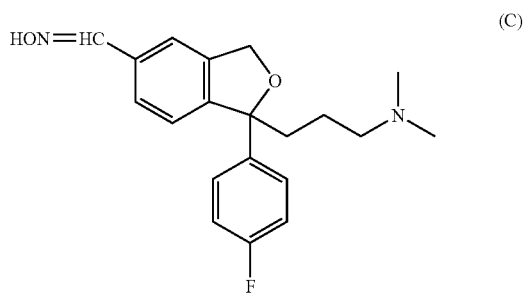

(C)

into citalopram by treatment with acetic anhydride. According to this document, the starting bromo derivative is obtained as described in GB 1,526,331 (corresponding to the Belgian patent 850,401), namely by submitting the 5-bromophthalide to a double Grignard reaction, said 5-bromophthalide being not indifferent to said reactants and being thus able to give rise to reaction by-products.

Literature discloses various routes of synthesis for preparing citalopram which either substantially reproduce the above-mentioned schemes or, alternatively, comprise a first Grignard reaction, the reduction and cyclization of the intermediate ketone and, finally, the introduction of the 3-dimethylaminopropyl chain by alkylation (WO 98/19511).

In general, the known syntheses use starting materials which are substituted by cyano (EP 171943), halo (WO 00/11926), amino (WO 98/19512), aminocarbonyl or alkoxycarbonyl (WO 98/19513), oxazolino or thiazoline (WO 00/23431) groups as precursors of the cyano group of citalopram.

It has now surprisingly been found a simple and practical, alternative route for synthesizing citalopram from a different precursor, namely from 1-oxo-1,3-dihydro-5-isobenzofuran-carboxaldehyde, hereinafter also referred to as 5-formylphthalide, through the preparation of an inert under the conditions of a Grignard reaction, O-substituted oxime which, when submitted to the two Grignard reactions in sequence and to cyclization, affords an O-substituted 1-[3-(dimethylamino)propyl]-1-(4-fluorophenyl)-1,3-dihydro-5-isobenzofurancarbaldoxime which can easily give citalopram, as outlined in FIG. 1.

Thus the present invention, according to one of its embodiments, provides a process for the preparation of citalopram characterized by:

(a) treating 5-formylphthalide of formula

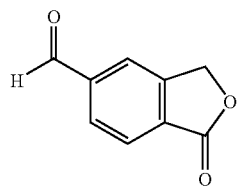

(I)

with a hydroxylamine of formula

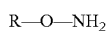 (II)

wherein R represents a hydrogen atom (IIa) or a substituent R' inert under the conditions of a Grignard reaction (IIb);

(b) reacting the oxime thus obtained of formula (III)

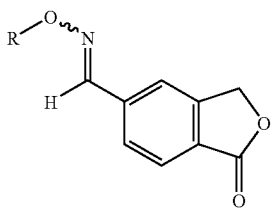

wherein R is as defined above, with a 4-fluorophenylmagnesium halide, straightforwardly when R=R' (IIIb) or after substitution of R by R' when R=H (IIIa);

(c) reacting the intermediate ketone of formula (IV)

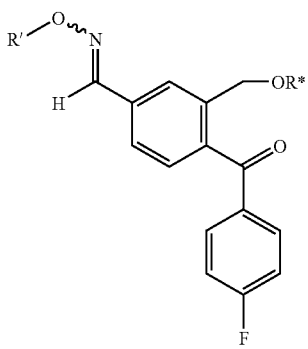

wherein R' is as defined above and R" represents MgHal (IVa) wherein Hal is halogen, or hydrogen (IVb), with a [3-(dimethylamino)propyl]magnesium halide;

(d) cyclizing the intermediate diol of formula (V)

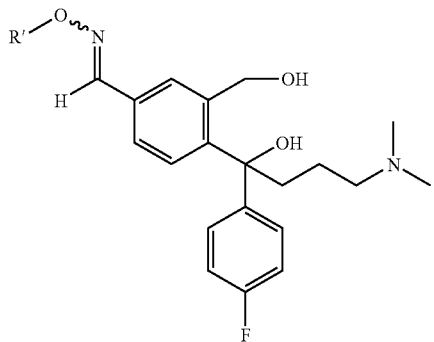

wherein R' is as defined above;

(e) removing the group R' of the substituted oxime of formula (VI)

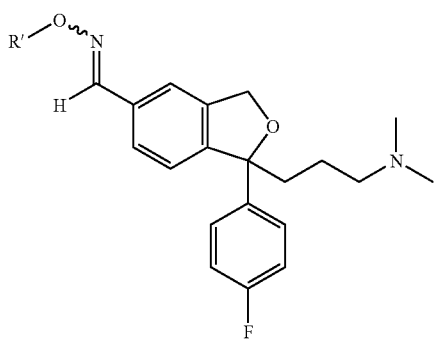

wherein R' is as defined above; and (f) converting the unsubstituted oxyimino group of the oxime of formula (VII)

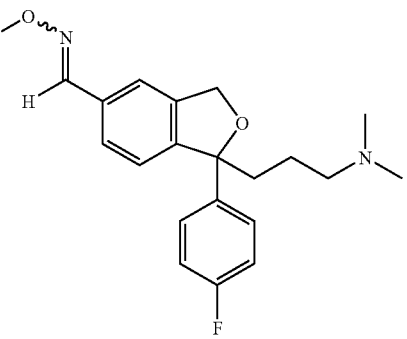

into a nitrile group to give citalopram (A) or one of its pharmaceutical acceptable salts; or (e') alternatively, when R' is triphenylmethyl or diphenylmethyl, straightforwardly converting the substituted oxyimino group of the compound of formula VI into a nitrile group by treatment with a mixed anhydride of formula

H—CO—O—CO—R'''  (VIII)

wherein R''' represents a $C_1$–$C_6$ alkyl group, an aralkyl group or an aryl group, to give citalopram (A) or a pharmaceutical acceptable salt thereof.

According to the present invention, in step (a) 5-formylphyhalide of formula I is reacted with a hydroxylamine of formula II.

The starting 5-formylphthalide is a known compound, obtainable for example as described in J. Chem. Soc., 1925, 2279–2290 or by hydrogenation of 5-chlorocarbonylphthalide as illustrated in the experimental part of the present application.

The hydroxylamine II according to the present invention may be O-substituted (IIb, R=R') or unsubstituted (IIa, R=H).

The O-substituted hydroxylamines of formula IIb (R=R') may be easily prepared according to conventional literature methods. The most common ones, in particular the O-triphenylmethoxyamine, are normally commercial products.

The substituent R' of the O-substituted hydroxylamine can be whatever substituent, provided that it is inert under the conditions of a Grignard reaction, such as a ($C_1$–$C_6$) alkyl, ($C_1$–$C_3$)alcoxy($C_2$–$C_4$)alkyl or, advantageously, a benzyl a diphenylmethyl or triphenylmethyl group, unsubstituted or substituted on the benzene rings with one or more groups independently chosen among ($C_1$–$C_6$)alkyl, ($C_1$–$C_3$) alcoxy and nitro groups or with a 2,3- or 3,4-methylenedioxy group.

Preferably, R' is an optionally substituted triphenylmethyl or diphenylmethyl group.

In step (a), the reaction of 5-formylphthalide I with the O-substituted hydroxylamine IIb, as such or as a salt thereof such as hydrochloride or hydrobromide, is carried out in an organic solvent, for example a hydrocarbon such as cyclohexane, toluene, xylene, dichloromethane, or an ether such as methyl-t-butylether, tetrahydrofuran or dioxane, or a dipolar aprotic solvent such as dimethylacetamide. The hydroxylamine of formula II is generally used in a molar ratio comprised between 1:1 and 2:1, preferably of 1.1:1 in respect of 5-formylphthalide.

When the hydroxylamine (IIb) is in form of a salt thereof it is suitable to operate in the presence of an organic base such as trimethylamine or triethylamine, preferably in a 5÷10% molar excess in respect of the used hydroxylamine salt Generally, when R═R', after sting the reaction mixture at a temperature of from 20° C. to the reflux temperature, the O-substituted 1-oxo-1,3-dihydro-5-isobenzofurancarbaldoxime (IIIb) is isolated according to conventional techniques, for example by evaporating a part of the solvent, diluting the reaction mixture with water and isolating the precipitated product which can be converted into a salt thereof, for example the hydrochloride or the hydrobromide.

On the contrary, when in step (a) 5-formylphthalide is reacted with unsubstituted hydroxylamine (IIa, R═H) in form of a salt, the unsubstituted oxime IIIa (R═H) is obtained In such a case, before carrying out the Grignard reactions, it is preferred to suitably protect the free hydroxyl with a group R', thus obtaining the protected oxime IIIb (R═R').

Generally, the hydroxylamine as a salt and the 5-formylphthalide are made to react, usually at room temperature, in a molar ratio comprised between 2:1 and 1:1, preferably of 1.1:1, in an aprotic solvent such as for example dimethylformamide and in the presence of a base such as triethylamine. Then, there is proceeded to the isolation of the compound IIIa (R═H), generally by precipitation with water, and to the subsequent substitution on the oxime to give IIIb (R═R'). Usually, the oxime IIIb and the reactant R'—X, wherein X is a leaving group, i.e. a halide, preferably a chloride, or a sulfonate, are dissolved in a solvent such as for example tetrahydrofuran in the presence of a base such as for example potassium t-butylate, potassium carbonate or pyridine, generally at room temperature.

The oximes of formula III prepared according to the above described step (a), and in general the oximes derived therefrom according to the present process, of formula IV, V, VI, and VII, may indifferently be obtained in form of one of their regioisomers E and Z or of mixtures thereof.

In steps (b) and (c), the compound of formula IIIb (R═R') thus obtained is submitted to two Grignard reactions in sequence. In particular, the compound of formula IIIb is reacted with a 4-fluorophenylmagnesium halide, preferably the bromide, under the usual conditions of a Grignard reaction, using ethers, preferably tetrahydrofuran, or their mixtures with aromatic solvents such as toluene, as a solvent, by adding the reactant at a temperature of from −20 to about 20° C., preferably at about 15° C. The 4-fluorophenylmagnesium halide is generally used in a molar ratio comprised between 1.3:1 and 1:1, preferably of 1.2:1, in respect of the oxime of formula IIIb.

When the starting material IIIb has reacted, approximately after about 10÷15 hours under stirring, the reaction mixture, containing the magnesium derivative of formula IVa, wherein R' is as defined above and Hal represents a halogen, preferably bromine, is treated, generally straightforwardly, with a [3-(dimethylamino)propyl]magnesium halide, preferably the chloride, dissolved in the same solvent used for the previous Grignard reaction, preferably tetrahydrofuran, again under the usual conditions of a Grignard reaction (step (c)). The [3-(dimethylamino)propyl]magnesium halide is generally used in a molar ratio comprised from 1.5:1 to 1:1, preferably comprised between 1.3:1 and 1.1:1 in respect of the oxime of formula IIIb.

Thus, there is obtained a magnesium derivative having the formula

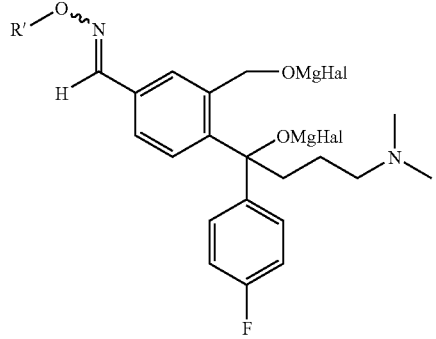

(Va)

wherein R' is as defined above and Hal represents a halogen, which is usually decomposed in situ in slightly acidic, preferably by acetic acid, medium or by treatment with aqueous ammonium chloride.

Thus, there is obtained a solution containing the diol of formula V, wherein R' is as defined above, which can be isolated, as such or as a salt thereof, according to the conventional techniques or transformed into the corresponding free oxime by removal of the group R' according to the classical methods depending upon the nature of said group (R'═H, Vb).

Alternatively, the solution containing the compound of formula V may be straightforwardly submitted to the subsequent step (step d).

In step (d), the cyclization of the compound V thus obtained is generally carried out by an elimination reaction, for example by formation of an active monoester of the diol, advantageously by treatment of said diol with an alkyl or arylsulfonylchloride to give a sulfonate such as the p-toluenesulfonate or, preferably, the methanesulfonate, which behaves as a leaving group removable in alkaline medium, for example by treatment with an alkaline hydroxide or with a tertiary base such as trimethylamine, triethylamine, N-methylpiperidine or N-methylmorpholine to give the O-substituted 1-[3-(dimethylamino)propyl]-1-(4-fluorophenyl)-1,3-dihydro-5-isobenzofurancarbaldoxime of formula VI, wherein R' is as defined above, which is generally isolated in yields higher than 90%.

The sulfonating agent is generally used in a molar ratio comprised between 4:1 and 1:1, preferably between 2.5:1 and 1.5:1 in respect of the diol of formula V. The base is generally employed in an excess in respect of the sulfonating agent, preferably in a molar ratio of about 2:1.

In step (e), the protective group R' is removed according to conventional methods to give the 1-[3-(dimethylamino)propyl]-1-(4-fluorophenyl)-1,3-dihydro-5-isobenzofurancarbaldoxime of formula VII which can be easily converted to citalopram (step (f)) for example by treatment with acetic anhydride, as described in the patent application WO 01/02383.

The method of removal of the used substituents R' are generally conventional methods, as those described in T. Green, P, Wuts, "Protective Groups in Organic. Synthesis", 3$^{rd}$ Ed., Wiley Interscience.

For example, when R' is an alkyl or an alkoxyalkyl group, in particular a methyl group, there generally operates under strongly acidic conditions.

When R' is diphenylmethyl or triphenylmethyl, the removal preferably occurs with formic acid. On the contrary, when R' represents benzyl, the removal by catalytic hydrogenation is preferred.

However, the preferred protective groups, namely the triphenylmethyl and diphenylmethyl groups, surprisingly and advantageously allow a direct conversion of the intermediate of formula VI into citalopram (step (e')).

In particular, when the substituent R' is the triphenylmethyl or diphenylmethyl group, the preparation of citalopram starting from 5-formylphthalide can occur in only four or, at most, five steps which allow the isolation of citalopram in very satisfactory purity conditions and in very good yields.

Thus, it is a preferred object of the present invention to provide a process for the preparation of citalopram and of its pharmaceutically acceptable salts, characterized by (i) treating 5-formylphthalide I with the O-triphenylmethyloxyamine of formula IIb, (R'=triphenylmethyl) or, alternatively, at first with hydroxylamine (IIa) and subsequently with an awaiting agent R'—X, in which R' represents triphenylmethyl;

(ii) submitting the O-triphenylmethyl-1-oxo-1,3-dihydro-5-isobenzofurancarboxaldoxime thus obtained of formula IIIb (R'=triphenylmethyl) to two subsequent Grignard reactions, the first one with a 4-fluorophenylmagnesium halide and the second one with a [3-(dimethylamino)propyl]magnesium halide;

(iii) sequentially treating the O-triphenylmethyl-3-hydroxymethyl-4-[α-hydroxy-α-[3-dimethylamino)propyl]-4-fluorobenzyl]benzaldoxime thus obtained of formula V (R'=tri phenylmethyl), with an alkyl- or arylsulfonyl chloride to give an active monoester of the diol, which is treated in an alkaline medium;

(iv) reacting the O-triphenylmethyl-1-[3-dimethylamino)propyl]-1-(4-fluorophenyl)-1,3-dihydro-5-isobenzofurancarboxaldoxime thus obtained of formula VI (R'=triphenylmethyl) with a mixed anhydride of formula VIII wherein R''' represents a $(C_1–C_6)$alkyl group, an arylalkyl group or an aryl group, to give citalopram (A) or a pharmaceutically acceptable salt thereof.

Steps (i) and (ii) are carried out as described above for steps (a) and (b), starting from 5-formylphthalide and O-triphenylmethyloxyamine IIb (R'=triphenylmethyl) or, alternatively, from 5-formylphthalide, hydroxylamine and, subsequently, an alkylating agent R'—X (R'=triphenylmethyl) and the product of formula IIIb (R'=triphenylmethyl) is isolated in very good yields.

In step (iii) the cyclization of the diol of formula V (R'=triphenylmethyl) occurs preferably by treatment with methanesulfonyl chloride and transformation into a monoester thereof and, subsequently, by reaction with bases, elimination of methanesulfonic acid and closing of the ring, in a manner analogous to what illustrated for step (d).

In the specific case in which the leaving group is methanesulfonyloxy, it has been observed that the cyclized product of formula VI (R'=triphenylmethyl) is generally present in an amount not lower than 80%, already at the end of the addition of said methanesulfonyl chloride.

At this point, in accordance with step (iv), the solvent is generally evaporated, the mixed anhydride VIII is added to the residue and the mixture is heated until the reaction is over.

Generally, the anhydride of formula VIII is used in great excess, preferably as reaction solvent The mixed anhydrides of formula VIII may be prepared according to usual methods, for example by treating a formic acid salt such as an alkaline formate, preferably sodium formate, with a halide, preferably the chloride, of the other carboxylic acid R'''—COCl and isolating the thus obtained mixed anhydride.

Alternatively, the mixed anhydrides VIII may be prepared by mixing equimolecular amount of formic acid and of the anhydride of the other carboxylic acid $(R'''—CO)_2O$ thus obtaining a mixture of the mixed anhydride VIII with the corresponding carboxylic acid R'''—COOH. When the acid R'''-COOH, its anhydride or its chloride are solid products, the preparation of the mixed anhydrides VIII may be carried out in an anhydrous organic solvent such as a hydrocarbon like cyclohexane, toluene, xylene, dichloromethane, or an ether such as methyl-t-butylether, tetrahydrofuran or dioxane.

Preferred mixed anhydrides of formula VIII are those in which R''' is a $(C_1–C_4)$alkyl, a benzyl or a phenyl group, more preferably R''' being methyl.

In fact, according to a particularly advantageous embodiment, as mixed anhydride formic-acetic anhydride, alone or in admixture with acetic acid or in the presence of a suitable solvent is used. The conversion into a nitrile with formic-acetic anhydride allows the direct obtainment of an easily isolable citalopram in a particularly pure form. In this last step triphenylmethanol acetate and formic acid are formed, that prevent the formation of undesired by-products such as, for example, the aldehyde or the corresponding free oxime.

In practice, it is possible to use formic-acetic anhydride previously prepared by treating sodium formate with acetyl chloride and distilling the thus obtained formic-acetic anhydride, or by refluxing a mixture of one mole of formic acid and, preferably, 1.25 moles of acetic anhydride for about one hour to obtain a mixture of formic-acetic anhydride and acetic acid. It can be advantageous to let the mixture thus obtained to cool to about 60° C. and adding it to the residue containing the cyclized intermediate VI (R'=triphenylmethyl) remained after the evaporation. Generally, the reaction mixture is heated at a temperature comprised between 80° C. and the reflux temperature, preferably at about 120° C.

Preferably, steps (iii) and (iv) above described, are carried out in sequence, without isolating intermediate compounds.

Typically, the diol of formula V (R'=triphenylmethyl) is treated with methanesulfonyl chloride in an organic solvent, for example a hydrocarbon such as cyclohexane, toluene, xylene or dichloromethane, or an ether, for example methyl-t-butylether, tetrahydrofuran or dioxane, in the presence of triethylamine by making a solution (preferably in the same solvent) of methanesulfonyl chloride to drop into the previously to 0÷5° C. cooled solution containing the diol V and the triethylamine, letting the mixture to stand for about 10÷30 minutes, evaporating the solvent, adding the previously prepared, as illustrated above, formic-acetic anhydride mixture, heating the reaction mixture at reflux for 2÷4 hours, then cooling to room temperature and letting the mixture to stand for a period indicatively of from 2 to 72 hours.

The citalopram obtained at the end of step (iv) is isolated according to conventional methods, by evaporating the solvent and purifying the residue, for example by treatment with water and extraction of impurities with an organic solvent Citalopram may be isolated as a free base by neutralizing the aqueous phase, extracting the free base with an organic solvent, recovering it after evaporation of the solvent and purifying it. The free base is preferably transformed and isolated in form of a pharmaceutically acceptable salt of citalopram, preferably the hydrobromide, by taking up the free base obtained after evaporation of the solvent; already sufficiently pure, with acetone, by adding to the obtained solution an aqueous solution of the desired acid, preferably 48% hydrobromic acid, evaporating the solvent and crystallizing the residue.

According to another embodiment, the present invention provides a process for the preparation of the 1-[3-(dimethylamino)propyl]-1-(4-fluorophenyl)-1,3-dihydro-5-isobenzofurancarboxaldoxime of formula VII and, optionally, of the corresponding 1-[3-(dimethylamino)propyl]-1-(fluorophenyl)-1,3-dihydro-5-isobenzofurancarbaldehyde, both described in WO 01/02383.

Such a process comprises submitting 5-formylphthalide I to the above steps, (a)–(e) and isolating the product thus obtained as such or in form of a salt thereof.

It is a further object of the present invention to provide a preparation of citalopram as a single enantiomer thereof. In fact, it is possible to obtain the single enantiomers of citalopram starting from the corresponding isolated enantiomers of the compounds of formula V or VI, prepared preferably by resolution with optical active acids, such as for example tartaric or camphorsulfonic acid, of the corresponding racemic mixtures of formula V and VI.

According to another aspect, the present invention provides new intermediates of formula III, IV, V and, respectively, VI, particularly useful in the synthesis of citalopram.

More particularly, the present invention provides new oximes of formula III, wherein R represents hydrogen or a substituent R' as hereinabove defined, and their salts. The compounds of formula III wherein R represents a substituent R' selected between triphenylmethyl and diphenylmethyl are particularly preferred.

The oximes of formula IIIb are useful not only in the direct synthesis of citalopram according to the process of the present invention, but also for the synthesis of 1-[3-(dimethylamino)propyl]-1-(4-fluorophenyl)-1,3-dihydro-5-isobenzofurancarbaldoxime of formula VII described in WO 01/02383. Such a synthesis according to the present invention is advantageous in respect to the known one; in fact, according to WO 01/02383 the 1-[3-(dimethylamino)propyl]-1-(4-fluorophenyl)-1,3-dihydro-5-isobenzofurancarbaldoxime, used as a precursor of citalopram, is prepared starting from a bromo derivative obtainable according to reactions which generate by-products difficult to eliminate.

Another aspect of the present invention is represented by the ketones of formula IV wherein R' represents a group inert under the conditions of a Grignard reaction as already defined or hydrogen and R" represents hydrogen or MgHal, wherein Hal is halogen.

The compounds of formula IV wherein R" is hydrogen may be isolated from the reaction mixture after step (b), for example by simple treatment of the magnesium intermediate with aqueous acids, even though, preferably, they are directly submitted to the subsequent Grignard reaction.

The compound of formula IV wherein R' represent hydrogen may be easily obtained by removal of the group R', wherein R' is a substituent inert under the conditions of a Grignard reaction, in accordance with the above-mentioned, classical deprotection methods. The compounds of formula IV wherein R' represents triphenylmethyl or diphenylmethyl are preferred.

It is a further object of the present invention to provide the intermediate diols of formula V and salts thereof, wherein R' represents a group inert under the conditions of a Grignard reaction, as hereinbefore defined, or hydrogen. Like the compound of formula IV, also the diol of formula V wherein R' is hydrogen may be prepared by simple removal of R' according to the traditional deprotection methods.

The preferred intermediate diols of formula V are those in which R' is diphenylmethyl or triphenylmethyl.

It is a final object of the present invention to provide the new oximes of formula VI, wherein R' is a group inert under the conditions of a Grignard reaction as defined above, other than methyl. The compounds of formula VI wherein R' represents triphenylmethyl or diphenylmethyl are preferred. The new oximes of formula VI may be easily converted to citalopram, preferably by a single step when R' represents triphenylmethyl or diphenylmethyl.

Furthermore, the oximes of formula VI are useful intermediates in the synthesis of 1-[3-(dimethylamino)propyl]-1-(4-fluorophenyl)-1,3-dihydro-5-isobenzofurancarboxaldoxime (VII) and, optionally, of 1-[3-(dimethylamino)propyl]-1-(4-fluorophenyl)-1,3-dihydro-5-isobenzofurancarboxaldehyde, both described in WO 01/02383.

According to a preferred embodiment of the process of the present invention, step (a) is carried out starting from 5-formylphthalide and an O-substituted hydroxylamine of formula IIb, optionally as a salt thereof in a molar ratio of about 1.1:1, at room temperature, in a solvent selected between dichloromethane and dimethylacetamide and, optionally, in the presence of an organic base such as triethylamine.

Alternatively, the oxime IIIb is prepared by reacting the unsubstituted hydroxylamine, as a salt thereof, triethylamine and 5-formylphthalide, in a molar ratio of 1.1:1, in dimethylformamide at room temperature, isolating the unsubstituted oxime IIIa (R=H) by precipitation with water and subsequently alkylating the oxime with triphenylmethyl chloride, in a molar ratio of about 1.15:1 in respect of the compound IIIa, in pyridine at a temperature of about 80° C. to give IIIb (R=R'=triphenylmethyl).

Step (b), namely the first Grignard reaction, is preferably carried out by slowly adding the 4-fluorophenylmagnesium bromide to the solution of the O-substituted compound of formula IIIb in tetrahydrofuran, in a molar ratio of 1.2:1 in respect of compound IIIb, at a temperature of about 15° C., preferably under inert atmosphere.

Step (c), namely the second Grignard reaction, is preferably carried out directly starting from the magnesium intermediate corresponding to the ketone of formula IV obtained in step (b), by adding the [3-(dimethylamino)propyl]magnesium chloride, dissolved in tetrahydrofuran, in a molar ratio with respect to compound IIIb comprised between 1.3:1 and 1.1:1 at a temperature around 5÷10° C., preferably under inert atmosphere.

Step (d), namely the cyclization reaction, is preferably carried out starting from the diol of formula V, isolated after treatment with aqueous ammonium chloride, by reaction with methanesulfonyl chloride in a molar ratio of about 2:1 in respect of the diol V, in the presence of triethylamine in a molar ratio of 4:1, at a temperature around 5÷7° C., in dichloromethane.

Step (e'), namely the direct conversion of the intermediate of formula VI, wherein R' represents triphenylmethyl or diphenylmethyl, into citalopram is preferably carried out on the residual raw material obtained after evaporation in step (d) by reaction with an excess of formic-acetic anhydride, heating at a temperature of about 120° C. for a period of time necessary to complete the reaction.

In order to better illustrate the invention without however, limiting it, the following example are presented.

The NMR spectra have been registered with a spectrophotometer Varian 300 MHz (Mercury) in solution of (DMSO)-$d_6$ or $CDCl_3$.

PREPARATION OF 5-FORMYLPHTHALIDE

In a hydrogenator, 23 l of N,N-dimethylacetamide, 1.65 Kg (8.39 moles) of 5-chlorocarbonylphthalide (prepared for example as described in J. Chem. Soc., 1931, 867–871) and 200 g of 5% Pd/BaSO$_4$ are charged Hydrogen is then charged at 3 bar thereinto and the mixture is heated at 60±3° C. for a total of 48 hours. The mixture is cooled and, after removal of the catalyst by filtration, the filtrate is concentrated under vacuum at 75° C. up to a solid residue. The product is dispersed with 8 l of deionized water and, at 5÷10° C. under stirring, the pH of the mixture is adjusted to 7.0÷7.5 by addition of 2.3 l of 10% ammonium hydroxide solution After a 30-minute stirring, the product is filtered, washed with deionized water and dried under vacuum at 50° C. to give 885 g (65%) of desired product having m.p.=163÷165° C. (in J. Chem Soc. 1925, page 2290 a m.p.=159÷160° C. is given).

$^1$H-NMR (DMSO-d$_6$) δ ppm: 5.51 (s, 2H, CH$_2$O), 8.00÷8.12 (m, 2H, arom.), 8.18 (s, 1H, arom.), 10.17 (s, 1H, CHO).

EXAMPLE 1

O-benzyl-1-oxo-1,3-dihydro-5-isobenzofurancarbaldoxime (IIIb, R'=benzyl)

To 81.07 g (0.5 moles) of 5-formylphthalide, prepared as described above, in 250 ml of 80% ethanol, 95.78 g (0.6 moles) of benzyloxyamine hydrochloride and 61.5 g (0.7 moles) of sodium acetate are added. The mixture is kept 30 minutes under stirring, than 100 ml of ethanol are distilled off. After cooling, the reaction mixture is diluted with 100 ml of water, filtered and dried under vacuum at 50° C. Thus, 125 g of O-benzyl-1-oxo-1,3-dihydro-5-isobenzofurancarbaldoxime are obtained (yield 93.5%).

$^1$H-NMR (DMSO-d$_6$) δ ppm: 5.15 (s, 2H, PhCH$_2$—O), 5.34 (s, 2H, CH$_2$—O lactone), 7.23÷7.25 (m, 5H, arom.), 7.71÷7.81 (m, 3H, phthalide), 8.41 (s, 1H, CH=N).

EXAMPLE 2

O-benzyl-3-hydroxymethyl-4-(4-fluorobenzyl)-benzaldoxime (IV, R'=benzyl)

A solution of 70.8 g (0.265 moles) of O-benzyl 1-oxo-1, 3-dihydro-5-isobenzofurancarbaldoxime in 450 ml of anhydrous tetrahydrofuran is cooled to −10° C. under nitrogen atmosphere, 81 g of a 14.5% solution of 4-fluorophenylmagnesium bromide (0.46 moles) are slowly added thereinto, by maintaining the temperature at −5÷−10° C., then the temperature of the solution is made to rise to 5° C. and the mixture is kept one hour at this temperature. The mixture is heated to 20° C. and kept under stirring at this temperature for 15 hours. After a check by HPLC of the disappearance of O-benzyl 1-oxo-1,3-dihydro-5-isobenzofurancarbaldoxime, the mixture is straightforwardly submitted to the next step.

EXAMPLE 3

O-Benzyl-3-hydroxymethyl-4-[α-hydroxy-α-[3-(dimethylamino)propyl]-4-fluorobenzyl]benzaldoxime (V, R'=benzyl)

The solution containing the magnesium derivative of the intermediate ketone (formula IV R'=benzyl) is cooled to −5° C. and slowly treated with 210 g of a 30% solution of [3-(dimethylamino)propyl]magnesium chloride (1.44 moles) in anhydrous tetrahydrofuran. The temperature of the solution is let to rise to 5° C. and, after a 1-hour stirring, the disappearance of the intermediate ketone is verified by HPLC. To the thus obtained solution, containing the magnesium derivative (formula V, R'=benzyl), brought to a temperature of 10÷15° C., 1500 g of a 15% aqueous solution of ammonium chloride are added and, after a 30-minute siring, the two phases are let to separate. The aqueous phase is twice extracted with 500 ml of toluene and the upper layer, consisting of a tetrahydrofuran solution, is diluted with 500 ml of deionized water, then the pH of the mixture is adjusted to 6 by addition of acetic acid and the tetrahydrofuran is evaporated off. The previous toluene extract is added to the residual aqueous phase, the mixture is kept under stirring and the pH is adjusted to pH 9 by addition of a 28% ammonium hydroxide solution. The phases are let to separate; the aqueous one is twice extracted with 150 ml of toluene, the organic phases are collected and the solution thus obtained is washed with an acidic aqueous diluted solution of acetic acid and then with water. A small portion of the organic phase is evaporated and submitted to NMR, the solution is directly used for the subsequent step.

$^1$H-NMR (CDCl$_3$) δ ppm: 1.45÷1.60 and 1.60÷1.75 (2m, 2H, CH$_2$—C—N); 2.20 (s, 6H, N(CH$_3$)$_2$); 2.25÷2.55 (m, 4H, CH$_2$—C—CH$_2$—N); 4.15 and 4.40 (2d, 2H, CH$_2$OH); 5.20 (s, 2H, CH$_2$Ph); 6.93 (pseudo t, 2H, H in ortho to F); 7.25÷7.60 (m, 10H, arom.); 8.11 (s, 1H, CH=N).

EXAMPLE 4

O-Benzyl-1-[3-(dimethylamino)propyl]-1-(4-fluorophenyl)-1,3-dihydro-5-isobenzofurancarbaldoxime (VI, R'=benzyl)

The toluenic solution of the O-benzyl-3-hydroxymethyl-4-[α-hydroxy-α-[3-(dimethylamino)propyl]-4-fluorobenzyl]benzaldoxime thus obtained (formula V, R'=benzyl) is concentrated under vacuum up to obtain a residue which is taken up with 1300 ml of dichloromethane. To the solution thus obtained 110 ml of triethylamine are added, the mixture is cooled to 5° C. and treated with a solution of 21.9 ml of methanesulfonyl chloride in 220 ml of dichloromethane. The temperature of the reaction mixture is let to rise to about 25° C., then the mixture is kept under stirring at the same temperature for two hours, cooled to 5° C. and its pH is brought to 8÷9 by addition of a 0.1N solution of sodium hydroxide. The phases are separated; the organic one is washed with deionized water, dried over anhydrous sodium sulphate and concentrated under vacuum. There are obtained 75.37 g of O-benzyl-1-[3-(dimethylamino)propyl]-1-(4-fluorophenyl)-1,3-dihydro-5-isobenzofurancarbaldoxime in form of an oil (yield 78.2%).

EXAMPLE 5

O-triphenylmethyl-1-oxo-1,3-dihydro-5-isobenzofurancarbaldoxime (IIIb, R'=triphenylmethyl)

To a suspension of 35 g of 5-formylphthalide (0.216 moles) in 800 ml of dichloromethane a solution of 65.4 g of triphenylmethyloxyamine (0.25 moles) in 350 ml of dichloromethane is added in 45 minutes. After about 2 hours at a temperature of 25÷27° C., the solution is concentrated under vacuum at 50° C. to a volume of about 100 ml, whereby the crystallization begins. To the mixture, 200 ml of methanol are added and the mixture is concentrated again, then a further volume of 300 ml of methanol is added an the solution is left to crystallize up to completion at 20÷25° C. After 2 hours a further volume of 400 ml of methanol is added, the dense mass is diluted with 300 ml of methanol and left 1 hour under stirring at 20÷25° C. The precipitate is filtered, washed with 100 ml of methanol and dried under vacuum. There are obtained 98 g of a white product consisting of O-triphenylmethyl-1-oxo-1,3-dihydro-5-isobenzofurancarbaldoxime in 90% purity. This product is suspended in 1 l of toluene and the suspension is heated 1 hour at reflux, then the possibly present insoluble part is eliminated by filtration in the warm, the solution is cooled at first to room temperature and subsequently to 0÷5° C. and kept for about 1 hour at this temperature. A further volume of 200 ml of toluene is added to the solution, then the precipitate is filtered and washed with 100 ml of toluene. Thus, 72.5 g of O-triphenylmethyl-1-oxo-1,3-dihydro-5-isobenzofurancarbaldoxime with a 95.1% (HPLC) purity are obtained. By concentration of the mother liquors to a little volume, a further amount of 10.9 g of product with a purity of 98.2% is obtained. Total weight 86.1 g (yield 90%).

$^1$H-NMR (CDCl$_3$) δ ppm: 5.23 (s, 2H CH$_2$O), 7.22÷7.40 (m, 15H, aroma. triphenylmethyl), 7.58 (m, 1H, arom., phthalide), 7.83 (d, 1H, arom. phthalide), 8.38 (s, 1H, CH=N).

By operating as described above, by using diphenylmethyloxyamine instead of triphenylmethyloxyamine, the O-diphenylmethyl-1-oxo-1,3-dihydro-5-isobenzofurancarbaldoxime is obtained.

EXAMPLE 6

1-Oxo-1,3-dihydro-5-isobenzofurancarboxaldoxime (IIIa, R=H)

To a suspension of 20 g (0.123 moles) of 5-formylphthalide and 9.4 g (0135 moles) of hydroxylamine hydrochloride in 100 ml of N,N-dimethylformamide, 17 ml (0.126 moles) of triethylamine are added in 20 minutes at 20÷22° C. The mixture is stirred for one hour, then the obtained suspension is poured in 700 ml of deionized water. After a 15-minute stirring it is filtered, the product is washed with water and dried under vacuum at 60° C. to give 18.85 g (yield 86%) of the desired product with a m.p.=208÷212° C.

$^1$H-NMR (DMSO-d$_6$) δ ppm: 5.40 (s, 2H, CH$_2$—O), 7.70÷7.90 (m, 3H, arom.), 8.30 (s, 1H, CH=N), 11.70 (s, 1H, OH).

EXAMPLE 7

O-triphenylmethyl-1-oxo-1,3-dihydro-5-isobenzofurancarboxaldoxime (IIIb, R'=triphenylmethyl)

A mixture of 2 g (0.011 moles) of 1-oxo-1,3-dihydro-5-isobenzofurancarboxaldoxime and 4.72 g (0.017 moles) of triphenylchloromethane in 40 ml of pyridine is heated at 80° C. for 5 hours, then it is concentrated under vacuum at 60° C. The residue is treated with 100 ml of deionized water, then the mixture is concentrated again and 200 ml of methanol are added to the residue. After a 15-hour stirring at room temperature, the product is filtered, washed with methanol and dried under vacuum at 60° C. to give 4.42 (yield 89%) of O-triphenylmethyl-1-oxo-1,3-dihydro-5-isobenzofurancarboxaldoxime.

$^1$H-NMR (CDCl$_3$) δ ppm: 5.23 (s, 2H CH$_2$O), 7.22÷7.40 (m, 15H, arom. triphenylmethyl), 7.58 (m, 1H, arom. phthalide), 7.83 (d, 1H, arom. phthalide), 8.38 (s, 1H, CH=N).

EXAMPLE 8

O-triphenylmethyl-1-oxo-1,3-dihydro-5-isobenzofurancarboxaldoxime (IIIb, R'=triphenylmethyl)

A mixture of 2 g (0.011 moles) of 1-oxo-1,3-dihydro-5-isobenzofurancarboxaldoxime, 4.72 g (0.017 moles) of triphenylchloromethane, 3.90 g (0.028 moles) of micronised potassium carbonate and tetrabutylammonium bromide (catalytic amount) in 40 ml of acetonitrile is heated at reflux for 5 hours, then cooled to room temperature and treated with 100 ml of ethyl acetate and 100 ml of water. The phases are separated and the organic one is washed again with 100 ml of water. The collected organic phases are concentrated at 60° C. to a residue which is taken up with methanol, by evaporating the solvent several times and finally by letting the product in methanol to stand 2 hours under stirring at room temperature. The product is filtered, washed with methanol and dried in an oven at 60° C. Thus, 3.07 g of O-triphenylmethyl-1-oxo-1,3-dihydro-5-isobenzofurancarboxaldoxime, as a white solid with a 95% purity (HPLC), are obtained (yield 61%).

EXAMPLE 9

O-triphenylmethyl-3-hydroxmethyl-4-(4-fluorobenzoyl)-benzaldoxime (IVb, R'=triphenylmethyl)

To a solution of 25 g (0.06 moles) of O-triphenylmethyl-1-oxo-1,3-dihydro-5-isobenzofurancarboxaldoxime in 125 ml of tetrahydrofuran, 92.8 ml of a 14.5% solution of 4-fluorophenylmagnesium bromide (0.067 moles) in tetrahydrofuran are slowly added under nitrogen atmosphere, in 3.5 hours at 15° C. After a HPLC control to verify that the amount of residual starting material is less than 2% (area), a 15% aqueous solution of ammonium chloride is added to the mixture; the organic phase is separated and washed with deionized water, adjusting the pH to 5.5. The mixture is distilled under vacuum in order to eliminate the tetrahydrofuran and toluene is added to the residue adjusting the pH to 9.5 by addition of 15% aqueous ammonium hydroxide. The phases are separated, the aqueous one is extracted twice with toluene and the collected toluenic phases are concentrated under vacuum. The residue weighing 51 g contains the O-triphenylmethyl-3-hydroxymethyl-4-(4-fluorobenzyl)-benzaldoxime (in an amount of 33 g, yield 65%).

$^1$H-NMR (CDCl$_3$) δ ppm: 4.56 and 4.66 (2 brs, 2H, CH$_2$OH); 3.54 (brs, 1H, OH).

EXAMPLE 10

Citalopram (A)

To a solution of 2 g (0.0033 moles) of O-triphenylmethyl-3-hydroxymethyl-4-[α-hydroxy-α-[3-(dimethylamino)propyl]-4-fluorobenzyl]benzaldoxime in 22 ml of dichloromethane, 2.2 ml of triethylamine (0.016 moles) are added. The obtained solution is cooled at 0÷5° C. and, in 20 minutes, a solution of 0.6 ml of methanesulfonyl chloride (0.007 moles) in 40 ml of dichloromethane is added thereinto. After a 1-hour sting at 20° C., the end of the reaction is checked by HPLC, then the solvent is evaporated under vacuum at 40° C. up to obtain an oily residue corresponding to the O-triphenylmethyl-1-[3-dimethylamino)propyl]-1-(4-fluorophenyl)-1,3-dihydro-5-isobenzofurancarboxaldoxime.

$^1$H-NMR (CDCl$_3$) δ ppm: 1.15÷1.55 (2m, 2H, CH$_2$—C—N), 2.15 (s, 6H, N(CH$_3$)$_2$), 2.15÷2.35 (m, 4H, CH$_2$—C—CH$_2$—N), 5.08 (2d, 2H, CH$_2$—O), 6.93 (pseudo t, 2H, H in ortho to F), 7.20÷7.50 (m, 20H, arom.), 8.23 (s, 1H, CH=N).

A mixture of 58 ml of acetic anhydride and 20 ml of 95% formic acid is separately prepared by heating one hour at reflux, then cooling to about 60° C. This solution, containing the formic-acetic anhydride, is treated with the above residual oil. The mixture is heated at reflux for 3 hours and, by a HPLC control it is observed that, after the indicated period of time, the reaction is practically over. The mixture is cooled to about 60° C. and the solvent is evaporated under vacuum to obtain an oily residue which is taken up with 150 ml of deionized water. The mixture is extracted with 3×100 ml of ethyl acetate, then the phases are separated, the organic one is discarded and the collected aqueous phase, having a pH of 3.45, is neutralized with a saturated aqueous solution of $NaHCO_3$ to reach a pH=7.5. The mixture is extracted with 3×200 ml of ethyl acetate, the collected organic phases are concentrated under vacuum at about 60° to obtain 0.95 g of citalopram base with a purity (HPLC)=95.6% (yield 86%).

EXAMPLE 11

Citalopram (A)

(a) To a suspension of 35 g (0.216 moles) of 5-formylphthalide in 800 ml of dichloromethane, 800 ml of a solution of 65.4 g of triphenylmethyloxyamine (0.25 moles) in 350 ml of dichloromethane are added in 45 minutes. After about 2 hours at 25÷27° C., the obtained solution is concentrated at about 50° C. under vacuum to a volume of about 100 ml, whereby the crystallization of the product begins. A volume of 200 ml of methanol is added to the mixture, which is concentrated again to a little volume, then it is diluted with further 300 ml of methanol and let to stand at 20÷25° C. for 2 hours to complete the crystallization. A further volume of 700 ml of methanol is added to the thick Suspension, the mixture is stirred at 20÷25° C. for one hour, the product is filtered, washed with 100 ml of methanol and dried under vacuum at 40° C. to give 75.2 g of O-triphenylmethyl-1-oxo-1,3-dihydro-5-isobenzofurancarboxaldoxime with m.p.=203÷206° C. and purity (HPLC)= 95.1%. From the mother liquors, by concentration to a little volume, further 10.9 g of product having a purity of 98.2% (HPLC) are recovered, Total yield 86.1 g (90%).

$^1$H-NMR (CDCl$_3$) δ ppm: 5.23 (s, 2H, CH$_2$O), 7.22÷7.40 (m, 15H, aroma., triphenylmethyl), 7.58 (m, 1H, arom., phthalide), 7.83 (d, 1H, arom., phthalide), 8.38 (s, 1H, CH=N).

(b) To a solution of 25 g (0.06 moles) of O-triphenylmethyl-1-oxo-1,3-dihydro-5-isobenzofurancarboxaldoxime in 125 ml of tetrahydrofuran, 92.8 ml of a 14.5% solution of 4-fluorophenylmagnesium bromide (0.067 moles) in tetrahydrofuran are slowly added in 3,5 hours, at 15° C. and under nitrogen atmosphere. After a control by HPLC to verify that the unreacted starting material is lower than 2% (area), the mixture is slowly cooled to 10° C., then 65 ml of a 30% solution of [3-(dimethylamino)propyl]magnesium chloride (0.135 moles) in tetrahydrofuran are slowly added at 5÷10° C. thereinto. After a HPLC control showing that the content in diol is of 23.1 g, 1400 g of a 15% aqueous solution of ammonium chloride is added at 5÷10° C. to the mixture under stirring. Said mixture is stirred for 30 minutes, then the phases are separated. The aqueous phase is extracted with 150+130 ml of toluene, the organic phase is concentrated and the residue is finally taken up with 200 ml of toluene. The toluenic phases are collected, treated with 200 ml of deionized water and the pH is adjusted to 3.0 by addition of acetic acid. The phases are separated and the organic one is extracted with a mixture of 120 ml of acetic acid and 190 ml of deionized water. The aqueous phase containing the diol in form of its salt is collected and, under stirring, 300 ml of toluene are added thereinto, then the pH of the mixture is brought to about 10 by addition of 30% aqueous ammonium hydroxide. The phases are separated, the organic one is collected and the aqueous phase is extracted with 2×60 ml, of toluene. The collected toluenic phases are washed with 3×60 ml of deionized water. The organic phase is concentrated under vacuum at about 50° C. and 27.2 g (75%) of O-triphenylmethyl-3-hydroxymethyl-4-[α-hydroxy-α-3-(dimethylamino)propyl-4-fluorobenzyl] benzaldoxime as a whitish product with a purity (HPLC)= 94.5% are obtained $^1$H-NMR (CDCl$_3$) δ ppm: 1.45÷1.75 (2m, 2H, CH$_2$—CN), 4.07 and 4.31 (2d, 2H, CH$_2$O), 6.92 (pseudo t, 2H, H in ortho to F), 7.20÷7.40 (m, 20H, arom.), 8.22 (s, 1H, CH=CN).

(c) To a solution of 23.3 g (0.039 moles) of O-triphenylmethyl-3-hydroxymethyl-4-[α-hydroxy-α-3-(dimethylamino)propyl-4-fluorobenzyl]benzaldoxime in 260 ml of dichloromethane, 25.5 ml (0.18 moles) of triethylamine are added. The mixture is cooled to 5° C. and a solution of 6 ml of methanesulfonyl chloride in 300 ml of dichloromethane are slowly (in 3 hours) added thereinto, by keeping the temperature at 5÷7° C. After a control by HPLC showing a content in diol lower than 2%, 230 ml of 0.1N NaOH are added to the reaction mixture, by maintaining the temperature at 0÷5° C. The phases are separated, the organic phase is washed three times with a mixture of 200 ml of deionized water and 25 ml of a 20% solution of sodium chloride. The aqueous phase is discarded, the organic one is collected and concentrated under vacuum to a solid residue. Thus, 22.3 g (97%) of O-triphenylmethyl-1-[3-(dimethylamino)propyl]-1-(4-fluorophenyl)-1,3-dihydro-5-isobenzofurancarboxaldoxime as a pale yellow product with purity (HPLC)= 90.8%.

$^1$H-NMR (CDCl$_3$) δ ppm: 1.15÷1.55 (2m, 2H, CH$_2$—C—N), 2.15 (s, 6H, N(CH$_3$)$_2$), 2.15÷2.35 (m, 4H, CH$_2$—C—CH$_2$—N), 5.08 (2d, 2H, CH$_2$—O), 6.93 (pseudo t, 2H, H in ortho to F), 7.20÷7.50 (m, 20H, arom.), 8.23 (s, 1H, CH=N).

(d) A mixture of 640 ml of acetic anhydride and 220 ml of 98% formic acid is heated one hour at 110° C., then it is cooled to 60° C. and 17.6 g (0.03 moles) of O-triphenylmethyl-1-[3-(dimethylamino)propyl]-1-(4-fluorophenyl)-1,3-dihydro-5-isobenzofurancarboxaldoxime are added thereinto. The obtained mixture is heated at 120° C. for 5 hours. After a HPLC control showing a conversion into citalopram of 88.2% (area), the mixture is concentrated under vacuum at 60° C. to an oil which is taken up with 170 ml of ethyl acetate and 350 ml of deionized water (pH of about 4). The pH is adjusted to 2.1 by addition of about 10 ml of 10% HCl. The phases are separated, the aqueous one is extracted with 170 ml of ethyl acetate. The pH of the aqueous phase is brought to 8.5 by addition of about 45 ml of 10% aqueous ammonium hydroxide; 90 ml of toluene are added thereinto and the mixture is kept under stirring for 2 hours. The phases are separated and the aqueous one is extracted with 3×100 ml of toluene. The toluenic phases are collected and concentrated under vacuum at 50° C. to a solid residue which is taken up with 35 ml of dichloromethane and loaded on a SiO$_2$ column by elating with a dichloromethane/methanol=9/1 mixture. By concentration of the eluate, 7.1 g (73%) of citalopram base with purity (HPLC)=98.2% is obtained.

(e) To a solution of 7.1 g of citalopram base in 35 ml of dichloromethane a solution of 7 g of sodium metabisulphite in 25 ml of deionized water is added. The pH of the mixture is brought to 6.0 by addition of 5% aqueous ammonium hydroxide, then the organic phase is discarded, the aqueous one is brought to pH=7.0 by addition of sodium bicarbonate and extracted with 2×10 ml of toluene. The organic phases are concentrated under vacuum at 50° C. to give 6.9 g of citalopram base with purity (HPLC)=99.8% (area). These 6.9 g of citalopram base are dissolved in 30 ml of acetone and 48% HBr is added to the solution to a pH of 4÷5. The obtained solution is evaporated under vacuum and the residue is crystallized with acetone to give 5.6 g of citalopram hydrobromide with purity (HPLC)=99.4% (area) and m.p. 185÷187° C.

$^1$H-NMR (DMSO-$_6$) δ ppm: 1.30÷1.60 (m, 2H, C—C$_2$—C—N); 2.21 (t, 2H, CH$_2$—C—C—N); 2.66 (s, 6H, N(CH$_3$)$_2$); 3.01 (t, 2H, CH$_2$—N); 5.20 (2d, 2H, CH$_2$O); 7.18 (pseudo t, 2H, H in ortho to F); 7.55÷7.62 (dd, 2H, H in meta to F); 7.27÷7.83 (m, 3H, H arom., phthalide); 9.22 (br s, 1H, NH).

What is claimed is:

1. A process for the preparation of citalopram which comprises:

(a) treating 5-formylphthalide of formula

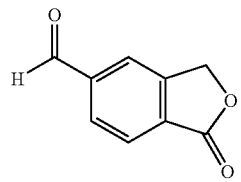
(I)

with a hydroxylamine of formula

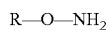
(II)

wherein R represents a hydrogen atom or a substituent R' inert under the conditions of a Grignard reaction selected from the group consisting of (C$_1$–C$_6$)alkyl, (C$_1$–C$_3$)alcoxy(C$_2$–C$_4$)alkyl, a benzyl, diphenylmethyl and triphenylmethyl group, unsubstituted or substituted on the benzene rings with one or more groups independently selected from the groups consisting of (C$_1$–C$_6$)alkyl, (C$_1$–C$_3$)alcoxy and nitro groups or with a 2,3- or 3,4-methylenedioxy group, to obtain an oxime of formula

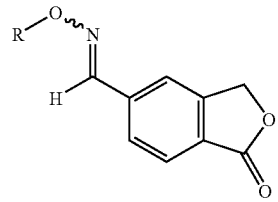
(III)

wherein R is as defined above;

(b) reacting the oxime thus obtained with a 4-fluorophenylmagnesium halide; when R=R' (IIIb) or after substitution of R by R' when R=H (IIIa) to form an intermediate ketone of formula

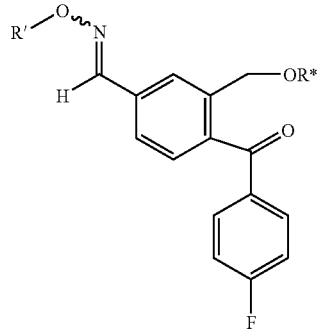
(IV)

wherein R' is as defined above and R" represents MgHal (IVa) wherein Hal is halogen, or hydrogen (IVb);

(c) reacting the intermediate ketone of formula IV with a [3-(dimethylamino)propyl]magnesium halide to form an intermediate diol of formula

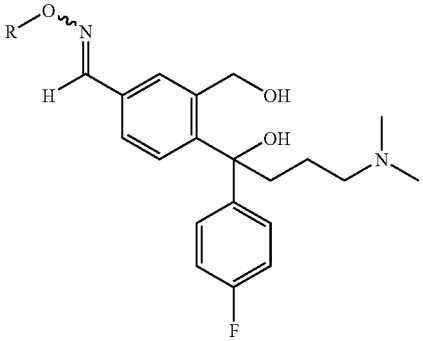
(V)

wherein R' is as defined above; and (d) cyclizing the intermediate diol of formula V to form a substituted oxime of formula

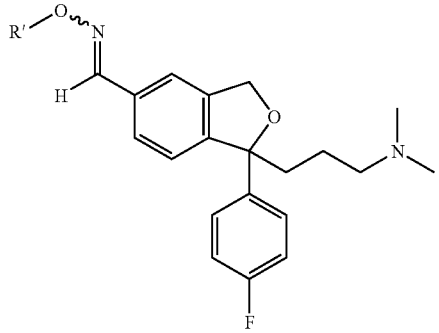
(VI)

wherein R' is as defined above;

(e) optionally, when R is not H removing the group R' of the substituted oxime of formula VI to form an unsubstituted oxyamino group of the oxime of formula

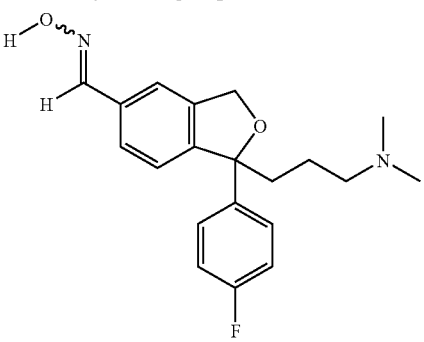
(VII)

(f) converting the unsubstituted oxyamino group of the oxime of formula VII into a nitrile group to give citalopram or one of its pharmaceutical acceptable salts; or (e') optionally, when R' is triphenylmethyl or diphenylmethyl, converting the substituted oxyamino group of the oxime of formula VI into nitrile by treatment with a mixed anhydride of formula

(VIII)

wherein R'" represents a C$_1$–C$_6$ alkyl group, an aralkyl group or an aryl group, to give citalopram or a pharmaceutical acceptable salt thereof.

2. A process according to claim 1 wherein R' is triphenylmethyl or diphenylmethyl.

3. A process according to claim 1 wherein said 4-fluorophenylmagnesium halide is the bromide.

4. A process according to claim 1 wherein said [3-(dimethylamino)propyl]magnesium halide is the chloride.

5. A process according to claim 1 wherein step (d) is carried out in the presence of a halide of an alkyl- or arylsulfonic acid.

6. A process according to claim 5 wherein said halide of an alkyl- or arylsulfonic acid is methanesulfonyl chloride.

7. A process according to claim 1 wherein R' represents triphenylmethyl or diphenylmethyl and the intermediate of formula VI is converted to citalopram according to step (e').

8. A process according to claim 7 wherein in said anhydride of formula VIII R''' represents ($C_1$–$C_4$) alkyl, benzyl or phenyl.

9. A process according to claim 8 wherein R''' represents methyl.

10. A process according to claim 9 wherein said anhydride of formula VIII is used in admixture with acetic acid.

11. A process according to claim 10 wherein said mixture is prepared from formic acid and acetic anhydride in a molar ratio of 1:1.25.

12. A process according to claim 1 wherein said compound of formula VIII is used in 1.25 moles per mole of compound of formula VI.

13. A process according to claim 1 wherein citalopram is isolated in the form of hydrobromide.

14. A process for preparing citalopram, according to claim 1, as a single enantiomer characterized in that the corresponding isolated enantiomers of the compounds of formula V or VI are used as intermediates.

15. A process according to claim 14, characterized in that the isolated enantiomers of compounds of formula V or VI are prepared by resolution of the corresponding racemic mixtures with an optically active acid selected from the group consisting of tartaric acid and camphosulfonic acid.

16. A process according to claim 14, characterized in that the isolated enantiomers of compounds of formula V or VI are prepared by resolution of the corresponding racemic mixtures with an optically active acid selected from tartaric or camphosulfonic acids.

17. The process of claim 1 where R' in formula III, represents hydrogen or a substituent R' inert under the conditions of a Grignard reaction.

18. The process of claim 1 where R' in formula III is triphenylmethyl or diphenylmethyl.

19. The process of claim 1 where R' in formula IV represents hydrogen or a substituent inert under the conditions of a Grignard reaction and R'' represents MgHal (IVa), wherein Hal is halogen, or hydrogen.

20. The process of claim 1 where R' in formula V represents hydrogen or a substituent inert under the conditions of a Grignard reaction.

21. The process of claim 1 where R' in formula VI represents a substituent inert under the conditions of a Grignard reaction, other than methyl.

22. The process of claim 1 where R' in formula VI is triphenylmethyl or diphenylmethyl.

* * * * *

Disclaimer

7,166,729 B2—Leone Dall'Asta, Milan (IT); Giovanni Cotticelli, Cernusco sul Naviglio (IT). PROCESS FOR THE PREPARATION OF 5-FORMYLPHTHALIDE. Patent dated January 23, 2007. Disclaimer filed February 10, 2012, by the inventors.

Hereby disclaims complete claims 1-22 of said patent.

(*Official Gazette, October 23, 2012*)